United States Patent
Imeshev (10) Patent No.: US 10,390,995 B2
(45) Date of Patent: Aug. 27, 2019

(54) SHORT PULSE LASER WITH ADJUSTABLE PULSE LENGTH

(71) Applicant: AMO Development, LLC, Santa Ana, CA (US)

(72) Inventor: Gennady Imeshev, Irvine, CA (US)

(73) Assignee: AMO Development, LLC, Santa Ana, CA (US)

( * ) Notice: Subject to any disclaimer, the term of this patent is extended or adjusted under 35 U.S.C. 154(b) by 174 days.

(21) Appl. No.: 15/348,858

(22) Filed: Nov. 10, 2016

(65) Prior Publication Data

US 2017/0119577 A1    May 4, 2017

Related U.S. Application Data

(63) Continuation of application No. 14/198,409, filed on Mar. 5, 2014, now abandoned.

(60) Provisional application No. 61/794,651, filed on Mar. 15, 2013.

(51) Int. Cl.
*A61F 9/008* (2006.01)
*A61B 18/20* (2006.01)

(52) U.S. Cl.
CPC ............ *A61F 9/0084* (2013.01); *A61B 18/20* (2013.01); *A61F 9/00825* (2013.01); *A61F 2009/0087* (2013.01); *A61F 2009/00872* (2013.01); *A61F 2009/00887* (2013.01); *A61F 2009/00889* (2013.01)

(58) Field of Classification Search
CPC .......... A61F 9/008–009; G02B 26/007; G02B 26/02085; H01S 5/0057; H01S 5/1212
See application file for complete search history.

(56) References Cited

U.S. PATENT DOCUMENTS

| 4,764,930 A | 8/1988 | Bille et al. |
| 5,549,632 A | 8/1996 | Lai |
| 5,984,916 A | 11/1999 | Lai |
| 5,993,438 A | 11/1999 | Juhasz et al. |
| 6,325,792 B1 | 12/2001 | Swinger et al. |

(Continued)

OTHER PUBLICATIONS

Cortes., http://www.dmphotonics.com/CORTES-800%2040%20TW%20web.pdf., Archived on Aug. 15, 2009 [online] [Retrieved on Mar. 10, 2016] Backdated Using he Internet webpage URL: https://web.archive.org/web/20090415000000, http://www.dmphotonics.com/CORTES-800%2040%20TW%20web.pdf.

(Continued)

*Primary Examiner* — Nathan J Jenness
(74) *Attorney, Agent, or Firm* — Johnson & Johnson Surgical Vision, Inc.

(57) ABSTRACT

Embodiments of this invention relate to a system and method for performing laser ophthalmic surgery. The surgical laser system configured to deliver a laser pulse to a patient's eye comprises a laser engine that includes a compressor configured to compress laser light energy received, the compressor comprising a dispersion or spectrum altering component provided on a computer controlled stage connected to a computing device. A user providing an indication of a desired pulse width received by the computing device causes the computing device to reposition the stage and the component provided thereon, resulting in a different pulse length being transmitted by the laser engine.

10 Claims, 6 Drawing Sheets

(56) References Cited

U.S. PATENT DOCUMENTS

| | | | |
|---|---|---|---|
| 2005/0226278 A1* | 10/2005 | Gu | H01S 3/0057 |
| | | | 372/6 |
| 2006/0159137 A1 | 7/2006 | Shah | |
| 2006/0207976 A1 | 9/2006 | Bovatsek et al. | |
| 2007/0129775 A1 | 6/2007 | Mordaunt et al. | |
| 2008/0004609 A1* | 1/2008 | Horvath | A61F 9/008 |
| | | | 606/4 |

OTHER PUBLICATIONS

Spitfire—TiSapphire Regenerative Amplifier Systems User's Manual. Spectra-Physics. Part No. 0000-255A, Rev, A. Aug. 2004.

* cited by examiner

SHORT PULSE LASER WITH ADJUSTABLE PULSE LENGTH

RELATED APPLICATION

This application is a continuation application under 35 USC § 120 of U.S. patent application Ser. No. 14/198,409, filed Mar. 5, 2014, now pending, which claims the benefit of priority to U.S. Provisional Patent Application No. 61/794,651, filed on Mar. 15, 2013, the entire disclosures of the above two applications are incorporated herein by reference.

BACKGROUND

Field

Embodiments of this present invention generally relate to laser systems, and more specifically, to the application of laser pulses during surgical procedures such as laser-assisted ophthalmic surgery.

Background

Eye surgery is now commonplace with some patients pursuing it as an elective procedure to avoid using contact lenses or glasses and others pursuing it to correct adverse conditions such as cataracts. Moreover, with recent developments in laser technology, laser surgery has become the technique of choice for ophthalmic procedures. Laser eye surgery typically uses different types of laser beams, such as ultraviolet lasers, infrared lasers, and near-infrared, ultra-short pulsed lasers, for various procedures and indications.

A surgical laser beam is preferred over manual tools like microkeratomes as it can be focused accurately on extremely small amounts of ocular tissue, thereby enhancing precision and reliability. For example, in the commonly-known LASIK (Laser Assisted In Situ Keratomileusis) procedure, an ultra-short pulsed laser is used to cut a corneal flap to expose the corneal stroma for photoablation with an excimer laser. Ultra-short pulsed lasers emit radiation with pulse durations as short as 10 femtoseconds and as long as 3 nanoseconds, and a wavelength between 300 nm and 3000 nm. Besides cutting corneal flaps, ultra-short pulsed lasers are used to perform cataract-related surgical procedures, including capsulorhexis, capsulotomy, as well as softening and/or breaking of the cataractous lens.

In laser surgery performed with an ultra-short pulsed laser, the laser engine is configured to deliver a laser beam with ultra-short pulse durations (which may be as long as a few nanoseconds or as short as a few femtoseconds) to a patient's eye. Temporal pulse profile and the pulse width are generally static in that they do not change during a procedure or during different phases of a procedure. Nor do they change when different procedures are performed separately, such as, for example, a capsulorhexis, a capsulotomy, lens fragmentation, corneal incisions, and the like.

Nevertheless, some issues may arise during different surgical procedures. As a specific example, certain types of ophthalmic incisions may require one type of laser profile, while another type of incision may benefit from a profile having a different pulse length. Conventional laser systems have a limited or non-existent ability to change the laser pulse profile. Where the ability is limited, the laser pulse may be changed to a desired profile, but only after one phase of a surgical procedure is completed with the initial profile. To change the laser's pulse profile, an operator must manually adjust the positions of certain system components, or make time consuming changes to the components themselves. Once this process is completed, the device may be powered on to commence another phase of the procedure. As may be appreciated, time delay is highly undesirable.

As such, there is a need for an ultra-short pulsed surgical laser system that overcomes the limited pulse profile capabilities available in conventional systems. In particular, it would be beneficial to offer a more robust ability to alter laser pulse profiles during laser-assisted refractive and cataract surgeries.

Embodiments of this invention include a surgical laser system and method for performing ophthalmic surgery. The laser system includes a laser engine configured to deliver a pulsed beam to a patient's eye, wherein the engine includes a compressor configured to compress laser light energy received, the compressor comprising a dispersion or spectrum altering component provided on a computer controlled stage connected to a computing device. A user provides an input to a computing device regarding a desired pulse width causes the computing device to reposition the stage and the component provided thereon, which results in a different pulse length to be transmitted by the laser engine.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

DETAILED DESCRIPTION

The drawings and related descriptions of the embodiments have been simplified to illustrate elements that are relevant for a clear understanding of these embodiments, while eliminating various other elements found in conventional collagen shields, ophthalmic patient interfaces, and in laser eye surgical systems. Those of ordinary skill in the art may thus recognize that other elements and/or steps are desirable and/or required in implementing the embodiments that are claimed and described. But, because those other elements and steps are well known in the art, and because they do not necessarily facilitate a better understanding of the embodiments, they are not discussed. This disclosure is directed to all applicable variations, modifications, changes, and implementations known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, brief summary, or the following detailed description.

Figure 1:
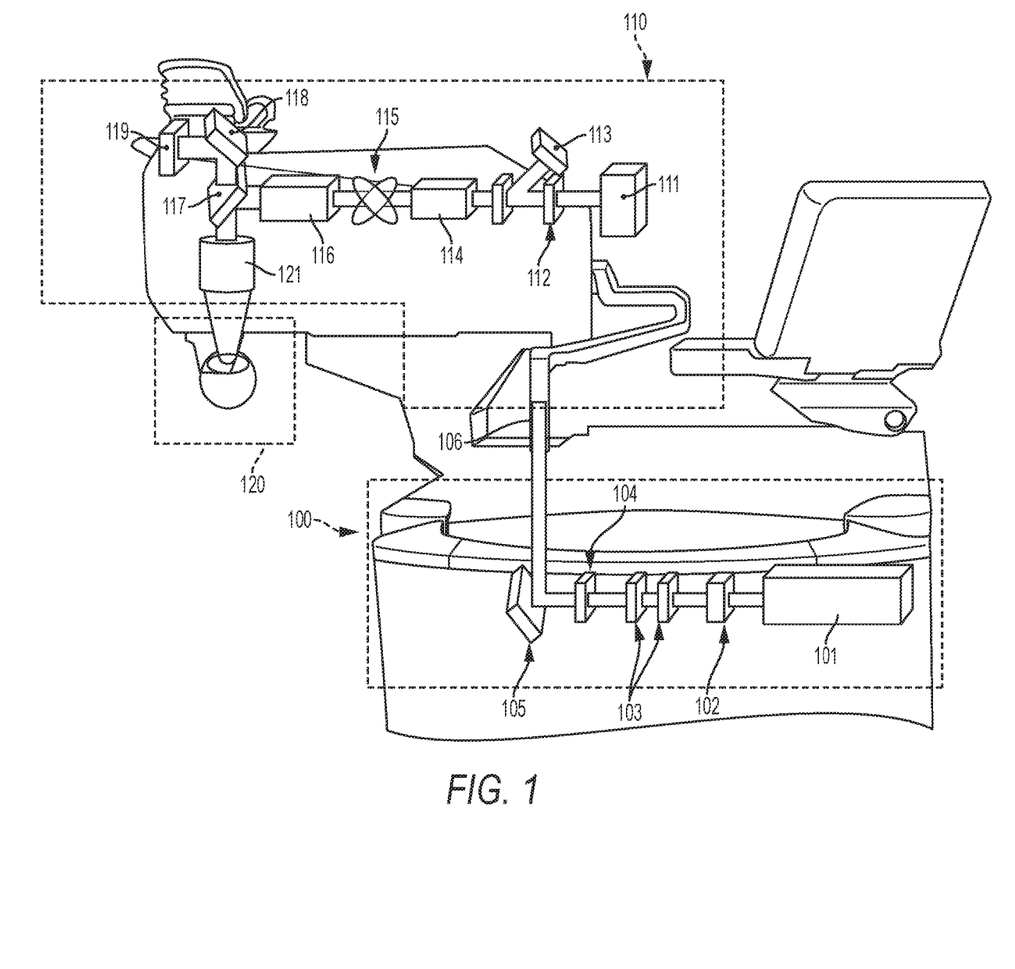
FIG. 1 illustrates a general overview of a non-UV, ultra-short pulse laser arrangement configured to employ the present design.

FIG. 1 illustrates a general overview of a laser arrangement configured to employ the present design. From FIG. 1, laser engine 100 includes laser source 101 and provides laser light to variable attenuator 102 configured to attenuate the beam, then to energy monitors 103 to monitor beam energy level, and first safety shutter 104 serving as a shutoff device if the beam is unacceptable. Beam steering mirror 105 redirects the resultant laser beam to the beam delivery device 110, through articulated arm 106 to range finding camera 111. The range finding camera 111 determines the range needed for the desired focus at the eye 120. Beam delivery device 110 includes second safety shutter 112 and beam monitor 113, beam pre-expander 114, X-Y (position) scanner 115, and zoom beam expander 116. Zoom beam expander 116 expands the beam toward IR mirror 117 which reflects and transmits the received beam. Mirror 118 reflects the received beam to video camera 119, which records the surgical procedure on the eye 120. IR mirror 117 also reflects the laser light energy to objective lens 121, which focuses laser light energy to eye 120.

In ophthalmic surgery using a pulsed laser beam, non-ultraviolet (UV), ultra-short pulsed laser technology can produce pulsed laser beams having pulse durations measured in the femtoseconds and picoseconds range. An exemplary ultra-short pulsed laser system shown in FIG. 1 can provide an intrastromal photodisruption technique for reshaping the cornea using a non-UV, ultra-short (e.g., femtosecond pulse duration), pulsed laser beam produced by laser source 101 that propagates through corneal tissue and is focused at a point below the surface of the cornea to photodisrupt stromal tissue at the focal point.

Although the system may be used to photoalter a variety of materials (e.g., organic, inorganic, or a combination thereof), the system is suitable for ophthalmic applications in one embodiment. The focusing optics, such as beam pre-expander 114, zoom beam expander 116, IR mirror 117 and objective lens 121, direct the pulsed laser beam toward an eye 120 (e.g., onto or into a cornea) for plasma mediated (e.g., non-UV) photoablation of superficial tissue, or into the stroma of the cornea for intrastromal photodisruption of tissue. In this embodiment, the system may also include a lens to change the shape (e.g., flatten or curve) of the cornea prior to scanning the pulsed laser beam toward the eye. The system is capable of generating the pulsed laser beam with physical characteristics similar to those of the laser beams generated by a laser system disclosed in U.S. Pat. Nos. 4,764,930 and 5,993,438, which are incorporated herein.

The ophthalmic laser system can produce an ultra-short pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam has a wavelength that permits the pulsed laser beam to pass through the cornea without absorption by the corneal tissue. The wavelength of the pulsed laser beam is generally in the range of about 300 nm to about 3000 nm, and the irradiance of the pulsed laser beam for accomplishing photodisruption of stromal tissues at the focal point is typically greater than the threshold for optical breakdown of the tissue. Although a non-UV, ultra-short pulsed laser beam is described in this embodiment, the pulsed laser beam may have other pulse durations and different wavelengths in other embodiments. Further examples of devices employed in performing ophthalmic laser surgery are disclosed in, for example, U.S. Pat. Nos. 5,549,632, 5,984,916, and 6,325,792, which are incorporated here by reference.

Figure 2:
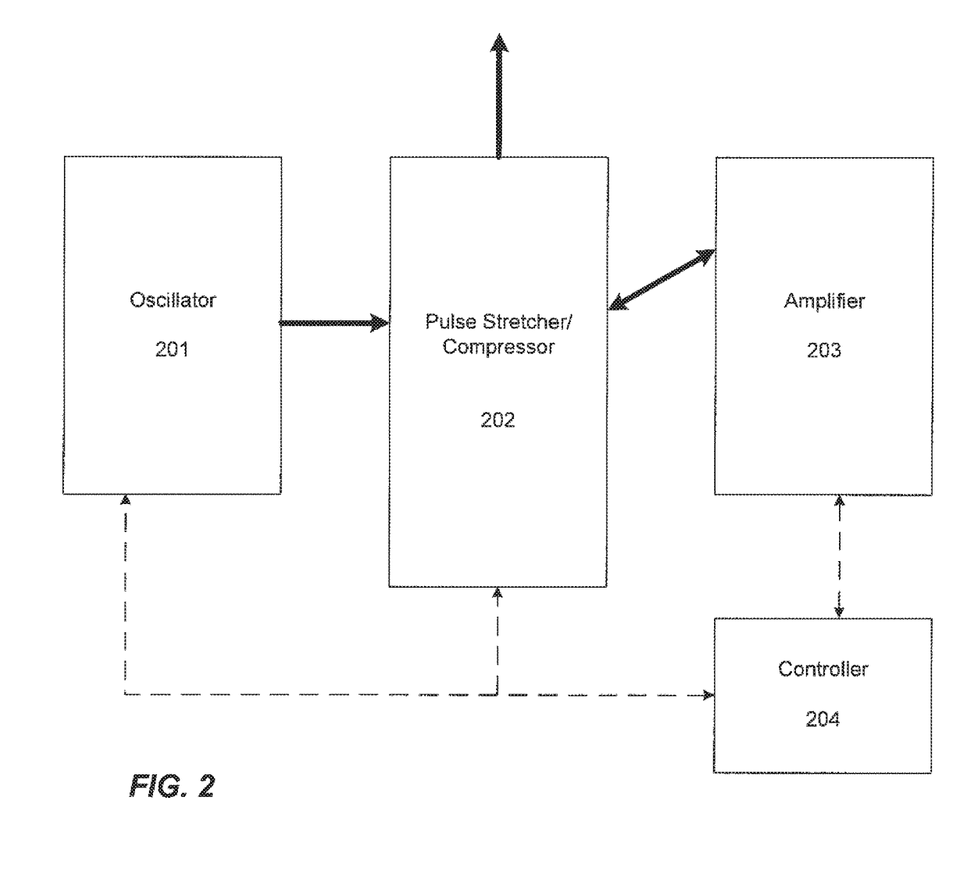
FIG. 2 is a general diagram of the components of a non-UV, ultra-short pulse bulk laser engine in an ophthalmic surgical laser system.

FIG. 2 illustrates general diagram of the components of a non-UV, ultra-short pulse laser engine in an ocular laser surgical system including laser engine 101. From FIG. 2, there is provided an oscillator 201, a beam stretcher/pulse compressor 202, and an amplifier 203. Controller 204 may be provided in the embodiments discussed herein. Lasers producing pulses in the femtosecond/picosecond duration range operate and generate pulses at high peak power levels, and if left unaltered can damage the gain medium. To address this issue, chirped pulse amplification (CPA) is employed wherein the length of pulses are extended or stretched to the picosecond range, resulting in a significant reduction in pulse peak power. From FIG. 2, the oscillator 201 generates and outputs a beam of femtosecond laser pulses. The pulse stretcher/compressor 202 extends the duration of the received pulses. Amplifier 203 increases amplitude of the pulses. The pulse stretcher/compressor then recompressed pulses to the femtosecond range prior to delivery.

Figure 3:
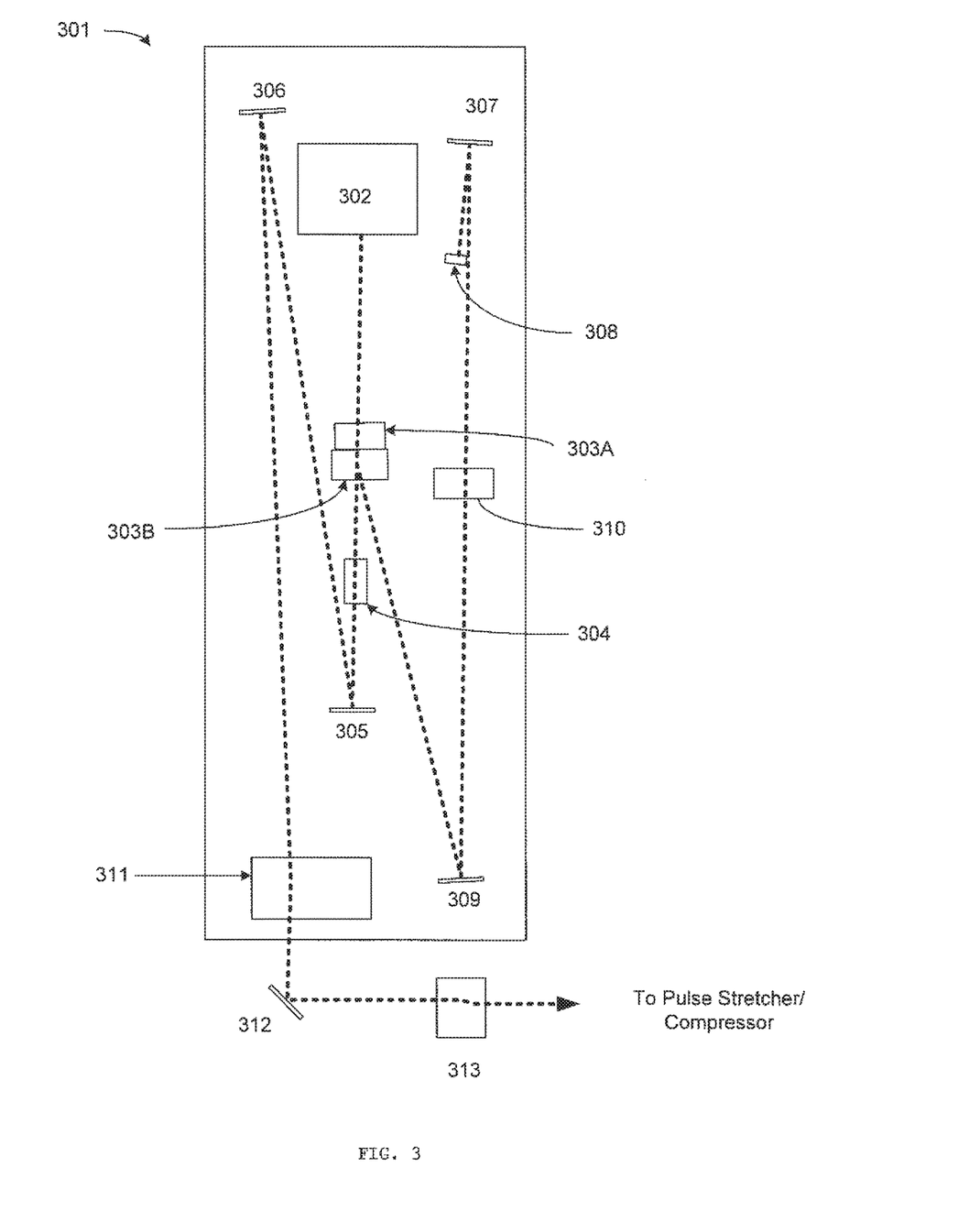
FIG. 3 illustrates a bulk oscillator that may be employed with the present design.

FIG. 3 illustrates an oscillator 301 used in a femtosecond bulk laser surgical device. Oscillator 301 includes laser pump 302 which directs laser light energy to focusing lens 303A and a dichroic mirror 303B, which both transmits the pump beam but reflects the cavity beam. In one path the cavity beam passes to mirror 309, aperture 310, mirror 307, and SESAM "HR" mirror 308. As used herein, the term "mirror" or "mirrors" is intended broadly to mean any type of reflective surface or surfaces. The other path from the dichroic mirror 303B is directed to oscillator glass assembly 304, horizontally polarized at Brewster's angle, to mirror 305, mirror 306, output coupler 311, and light energy ultimately passes out of oscillator 301 to mirror 312, beamsplitter 313, and pulse stretcher/compressor 202, not shown in this view.

Figure 4:
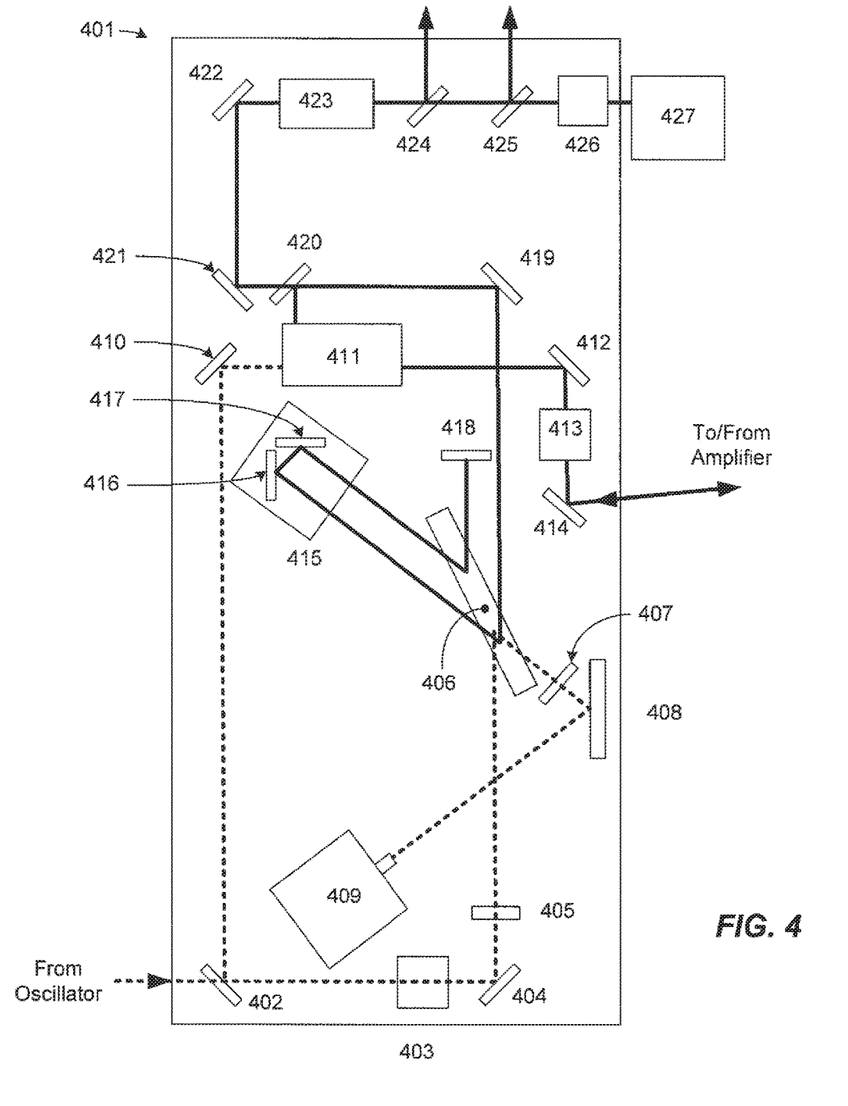
FIG. 4 is a pulse stretcher/compressor that may be employed with the present design.

FIG. 4 illustrates the components of pulse stretcher/compressor 401, which receives the beam under half mirror 402, with light passing to half wave plate 403, and one of a number of mirrors 404, over half mirror 405, to grating 406, stretcher lens 407, folding mirror 408, an stretcher mirror 409. The beam then travels through elements 408, 407 and 406 to half mirror 405 that reflects the beam back to another double-pass through the grating 406 and other elements. The beam then goes over half mirror 405 to elements 404 and 403. The beam is then gets reflected by half mirror 402 to reflective surface 410, which provides light energy to Faraday (three port) isolator 411, configured to receive and provide light energy to and from mirrors 412 and 420. As shown, mirror 412 provides light energy to half wave plate 413 and to an amplifier (not shown in this view). Light from half mirror 420 passes to mirror 419, grating 406, and to compressor retro-reflection assembly 415, including mirrors 416 and 417, back through grating 406 and to mirror 418. Light beam then passes through the grating 406, retro-reflection assembly 415, grating 406, to mirror 419. The light beam travels over half mirror 420 to mirror 421, to folding mirror 422, and to energy wheel 423, to beam splitters 424 and 425, fast shutter 426, and folding mirror to articulating arm 427. Light from beam splitters 424 and 425 are directed to the other components of the surgical system.

Figure 5:
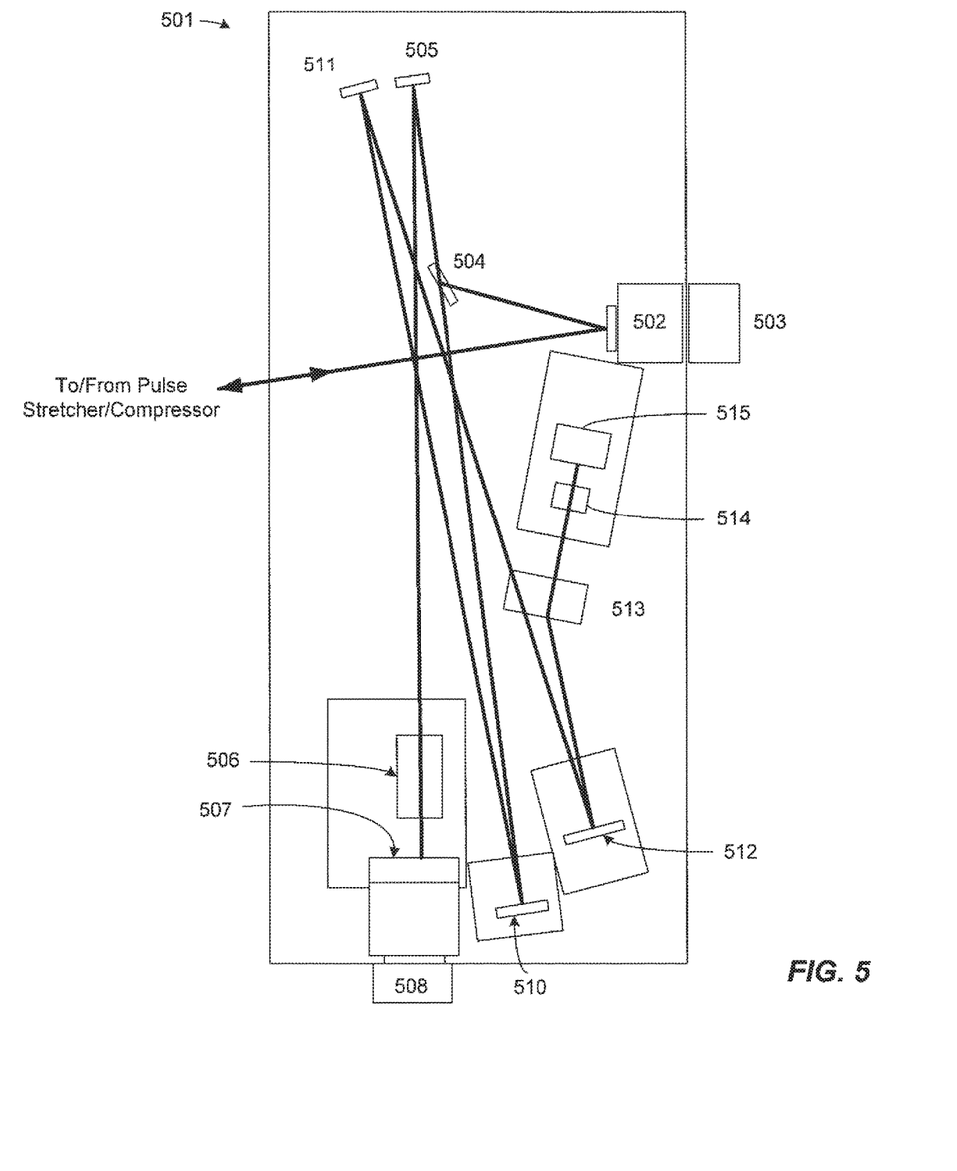
FIG. 5 shows an amplifier that may be employed with the present design.

FIG. 5 illustrates one embodiment of an amplifier 501 in accordance with the design of FIG. 2A, again including a number of mirrors as well as amp out photodiode 503, polarizer assembly 504, mirror 505, Pockels cell 506, mirror 507, and Q-switch photo diode 508. Also shown is a folding mirror 510, mirror 511, mirror 512 on a translation device, amplifier glass assembly 513, focusing lenses 514, and pump diode 515.

One embodiment of the present design employs the arrangement of FIGS. 3-5. Lasers may be employed in the ocular surgical environment to perform a variety of different cuts, such as corneal cuts, capsulotomy cuts, and lens fragmentation cuts. Each of these cuts is optimally performed using a different length pulse. For example, a corneal cut may use pulses in the 400-800 femtoseconds range, while lens fragmentation cuts may use pulses in the 1-5 picoseconds range. It would be advantageous to offer a surgeon an ability to achieve different pulse lengths when the surgeon switches from one desired pulse length to another desired pulse length with little effort required, unlike previous devices wherein extensive and/or manual component repositioning was required to alter pulse length.

The present design employs computer controlled adjustment of pulse length by changing the dispersion of the pulse compressor, pulse stretcher, or other components or assemblies in the beam path. Detuning the compressor from its optimal operating point tends to lengthen output pulses. One change of the design is to change the effective grating separation. This can be achieved by moving a stage 415a with mounted roof mirror 416-417 along the beam path indicated. In one embodiment, grating 406 may be repositioned, rotated, or otherwise altered to provide pulses of different lengths. Multiple components illustrated in FIG. 4 may be placed on stages and moved in a relatively short amount of time. As an example, the device may offer two different pulse lengths, and may offer two different positions for the various components. Components including but not limited to each of the reflective surfaces as well as one or more of grating 406, stretcher lens 407, folding mirror 408, and stretcher mirror 409, Faraday (three port) isolator 411, half wave plate 413, compressor retro-reflection assembly 415, folding mirror 422, energy wheel 423, fast shutter 426, and/or folding mirror to articulating arm 427 may be positioned on a stage or stages and may be translated and/or rotated to a desired second position to effectuate the second pulse length setting. Alternately, an alternate component may be switched in or out for an existing component to effectuate the second mode of operation. More positions and more pulse length options may be achieved by offering variable positioning of components. Alternatively, a pulse spectral shape or width may be altered (for example, by filtering spectral components within the stretcher or compressor) to adjust temporal pulse length.

Translation and/or rotation or substitution of components may be achieved using computer controlled motorized stages. During manufacturing or service, pulse length can be determined for more than one position or orientation of a given stage and the setting of both the stage and the resultant pulse length stored in computer memory. During surgery, the user may select a particular pulse length to achieve a particular cut, and the computer 204 may command the stage to translate or rotate or otherwise be repositioned to an available position to achieve desired pulse length.

A further alternative in FIG. 4 is to lengthen the distance between grating 406 and compressor retro-reflection assembly 415, which would lengthen the resultant pulses. Again, a computer controlled stage may be employed to effectuate the desired position of the components. A further alternative would be to substitute a second grating for grating 406, such that a computer controlled stage may substitute in and/or reposition a second grating (not shown) in place of and/or in a position differing from grating 406. Other components may be reoriented to effectuate a desired change in position.

While illustrated with respect to a bulk-grating compressor, the present design may be employed in other types of compressors, including prism based compressors wherein components such as mirror(s), prism(s), and so forth may be provided on stages and adjusted, moved, rotated, translated, or substituted to alter pulse length. Alternately, a grism, generally a combination between a grating and a prism, may be employed in the compressor, and grism components and components associated with the grism may be provided on stages and adjusted, moved, rotated, translated, or substituted using computer control to alter pulse length.

A further implementation may include a separate dispersion adjustment element added to a compressor, stretcher, or elsewhere in the beam path such as assembly 401 in FIG. 4, that adjusts dispersion either continuously or in steps. Use of a dispersion element can change the pulse width when employed with a compressor. Alternately, the dispersion adjustment element can provide a fixed level of dispersion when positioned in the beam path or no dispersion when removed from the beam path.

Figure 6:
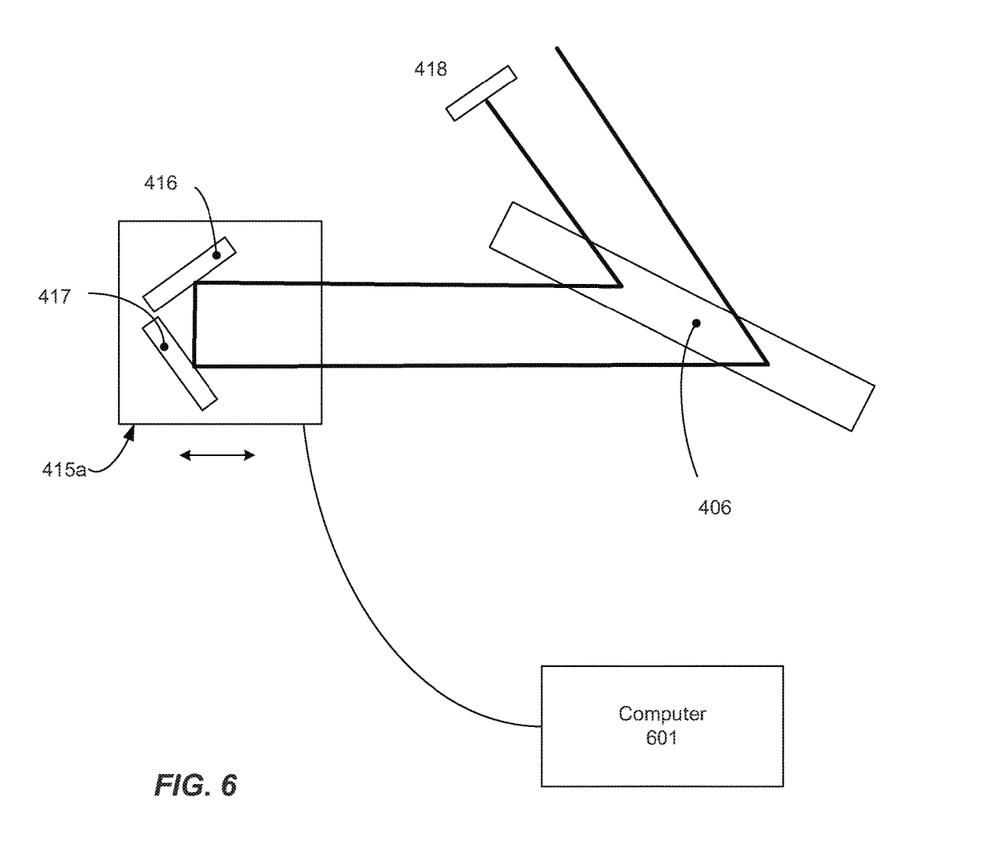
FIG. 6 is a conceptual illustration of a stage having a component positioned thereon usable with the present design.

FIG. 6 is a general representative drawing of a motorized stage that may be used with the design illustrated in FIG. 4 and includes components illustrated in FIG. 4. Mirrors 416 and 417 are root reflectors positioned on a motorized stage 415a configured to move toward and away from grating 406. Such movement tends to stretch or compress the pulses received. In the beam path illustrated, light passes to grating 406, mirror 416, mirror 417, back to grating 406, and to mirror 418, where it is reflected as a retro beam. Computer 601 controls the motorized stage to move in the direction shown.

Thus, the present design comprises offering a set of components in a laser engine compressor configured to be mechanically repositioned or replaced in order to alter pulse length of the resultant laser output. In one embodiment, at least one component is placed on a mechanical stage connected to a controller such that when a different pulse length is selected, the computer provides a command to move the stage and the component located thereon. Such movement alters the pulse width of the resultant pulse delivered to the patient in a surgical procedure such as a femtosecond laser ocular surgical procedure.

In another embodiment, multiple components may be repositioned, and in another embodiment, certain components may be replaced with other components or removed form or inserted into the beam path using computer control. Mechanical stages may be employed with any components in a pulse stretcher/pulse compressor or elsewhere in the beam path including but not limited to gratings, prisms, grisms, reflective surfaces or mirrors, half wave plates, lens assemblies or focusing lenses, retro-reflect assemblies, Faraday isolators, folding mirrors, half mirrors, energy wheels, and/or dispersion elements.

Those of skill in the art will recognize that the step of a method described in connection with an embodiment may be interchanged without departing from the scope of the invention. Those of skill in the art would also understand that information and signals may be represented using any of a variety of different technologies and techniques. Skilled artisans may implement the described functionality in varying ways for each particular application, but such implementation decisions should not be interpreted as causing a departure from the scope of the present invention. An apparatus implementing the techniques or components described herein may be a stand-alone device or may be part of a larger device.

Although embodiments of this invention are described and pictured in an exemplary form with a certain degree of particularity, describing the best mode contemplated of carrying out the invention, and of the manner and process of making and using it, those skilled in the art will understand that various modifications, alternative constructions, changes, and variations can be made in the ophthalmic interface and method without departing from the spirit or scope of the invention. Thus, it is intended that this invention cover all modifications, alternative constructions, changes, variations, as well as the combinations and arrangements of parts, structures, and steps that come within the spirit and scope of the invention as generally expressed by the following claims and their equivalents.

What is claimed is:

1. A method for generating a pulse laser beam to be delivered to a patient's eye, comprising:
   generating a beam of laser pulses by an oscillator, the laser pulses having a first pulse length;
   inputting the beam of laser pulses to a compressor;
   changing the pulse length of the input laser pulses by the compressor to output a beam of laser pulses having a second pulse length, the compressor comprising a plurality of optical components directing the beam of laser pulses along a beam path, including a moveable optical component mounted on a computer controlled stage, the moveable optical component being at a first position;
   focusing the beam of laser pulses having the second pulse length into a first tissue of the patient's eye to perform incisions in the first tissue;
   then, receiving a user instruction by a computing device, the user instruction specifying a third pulse length;
   in response to the user instruction, controlling the stage by the computing device to reposition the moveable optical component to a second position to output a beam of laser pulses having the third pulse length from the compressor; and
   focusing the beam of laser pulses having the third pulse length to a second tissue of the patient's eye to perform incisions in the second tissue, wherein the third pulse length is different from the second pulse length and the second tissue is different from the first tissue.

2. The method of claim 1, wherein the reposition of the moveable optical component includes a translation or a rotation.

3. The method of claim 1, further comprising:
   storing, in a memory of the computing device, a plurality of pulse lengths corresponding to a plurality of positions of the moveable optical component; and
   wherein the controlling step includes selecting from the memory one of the plurality of positions of the moveable optical component based on the user instruction and moving the moveable optical component to the selected position.

4. The method of claim 1, wherein the moveable optical component is a dispersion altering component.

5. The method of claim 4, wherein the dispersion altering component effectuates a first dispersion to the laser pulses when at the first position and effectuates a second dispersion to the laser pulses when at the second position.

6. The method of claim 4, wherein when at the first position, the dispersion altering component is located in the beam path of the laser pulses, and when at the second position, the dispersion altering component is removed from the beam path and the second dispersion is zero.

7. The method of claim 1, wherein the moveable optical component is a spectrum altering component.

8. The method of claim 1, wherein the moveable optical component is a compressor retro-reflection assembly disposed at a distance from a grating along the beam path, and wherein at the first and second positions, the compressor retro-reflection assembly is disposed at different distances from the grating.

9. The method of claim 1, wherein the laser pulses have a wavelength in the range of 300 nm to 3000 nm.

10. The method of claim 1, wherein the first tissue and the second tissue are selected from a group consisting of a cornea of the eye, a lens capsule of the eye, and a lens of the eye.

* * * * *